United States Patent [19]

Matsubara

[11] Patent Number: 5,008,119

[45] Date of Patent: Apr. 16, 1991

[54] METHOD OF USING MANGANESE TO PROTECT AN ANIMAL FROM RADIATION DAMAGE

[76] Inventor: Junko Matsubara, c/o Department of Epidemiology, School of Medicine, University of Tokyo, No. 3-1, Hongo 7-chome, Bunkyo-Ku, Tokyo 113, Japan

[21] Appl. No.: 62,180

[22] PCT Filed: Oct. 6, 1986

[86] PCT No.: PCT/JP86/00510

§ 371 Date: Aug. 10, 1987

§ 102(e) Date: Aug. 10, 1987

[87] PCT Pub. No.: WO87/02245

PCT Pub. Date: Apr. 23, 1987

[30] Foreign Application Priority Data

Oct. 14, 1985 [JP] Japan .................... 60-228536
Oct. 6, 1986 [JP] Japan .................... 61-236255

[51] Int. Cl.$^5$ .................................. A61K 33/32
[52] U.S. Cl. ............................ 424/639; 514/917
[58] Field of Search .................. 424/639, 641, 643; 514/494, 492, 917

[56] References Cited

U.S. PATENT DOCUMENTS

| | | | |
|---|---|---|---|
| 1,962,371 | 6/1934 | Torigian | 424/639 |
| 2,034,783 | 3/1936 | Torigian | 424/639 |
| 3,887,704 | 6/1975 | Lichtenstein | 424/641 |
| 4,349,536 | 6/1982 | Hausler . | |

FOREIGN PATENT DOCUMENTS

| | | |
|---|---|---|
| 43-6690 | 3/1968 | Japan . |
| 45-8871 | 3/1970 | Japan . |
| 46-2674 | 1/1971 | Japan . |
| 55-43754 | 11/1980 | Japan . |
| 56-15210 | 2/1981 | Japan . |
| 56-79622 | 6/1981 | Japan . |
| 57-18621 | 1/1982 | Japan . |
| 1153113 | 1/1968 | United Kingdom . |

OTHER PUBLICATIONS

Remington's Pharmaceutical Sciences 15th ed. (1975), pp. 968-970.
Kagaku et al., Function and Sod-Like Activity of Metallothionein, *Metallothionein and SOD Yakassei*, vol. 22, No. 2, Feb. 1984 (Tokyo).
Webb, M. et al., Functions of Metallothionein, *Biochem. Pharmacol.*, vol. 31, No. 2, pp. 137-142 (1982).
Karin, M., Metallothioneins: Proteins in Search of Function, *Cell*, vol. 41, pp. 9-10 (May, 1985).
Fuwa, K., Elements for Inducing and Not Inducing Metallothionein Biosynthesis, *Living Organisms and Heavy Metal*, pp. 190-191 (1981).
Ishida, N., Immunopotentiating Activities of OK-432, *Excerpta Medica*, (1986) (Japanese and English).
Tsukagoshi, S., Host-Mediated Antitumor Activity of Polysaccharides, With Special Reference to the Effect of PS-K. A Protein-Bound Polysaccharide Isolated From Basidiomycetes, *Cancer and Chemotherapy*, vol. 1, No. 2, pp. 251-257 (1974).

(List continued on next page.)

*Primary Examiner*—Stanley J. Friedman
*Assistant Examiner*—Raymond J. Henley, III
*Attorney, Agent, or Firm*—Christensen, O'Connor, Johnson & Kindness

[57] ABSTRACT

An antioxidative biophylactic agent containing a substance that can induce metallothionein production in human or animal body. Manganese or compounds thereof, *Streptococcus hemolyticus* which has been deprived of a streptolysin-S-yielding ability, and an extract from coriolus versicolor belonging to the family Polyporaceae, Basidiomycetes having a remarkable metallothionein-inducing ability in vivo, and an antioxidative biophylactic effect such as radiation damage protection can be obtained by administering these metallothionein-inducing substances.

4 Claims, 7 Drawing Sheets

OTHER PUBLICATIONS

Tsukagoshi, S., Basic Studies of Immunochemical Therapy Utilizing Polysaccharides, *Advances in Medicine*, vol. 91, No. 9, pp. 505-510 (Nov., 1974).

Onosaka, S. et al., A Simplified Procedure for Determination of Metallothionein in Animal Tissues, *Eisei Kagaku*, vol. 24, pp. 128-131 (1978).

Ohara, H., et al., Variations of Cellular Sulfhydryl Content During Cell Cycle of HeLa Cells and Its Correlation to Cyclic Change of X-Ray Sensitivity, *Exptl. Cell Res.*, vol. 58, pp. 182-185 (1970).

Modig, H. G. et al., Release of Thiols From Cellular Mixed Disulphides and Its Possible Role in Radiation Protection, *Int. J. Radiat. Biol.*, vol. 22, No. 3, pp. 257-268 (1971).

Boyd, S. C. et al., High Concentrations of Glutathione in Glandular Stomach: Possible Implications for Carcinogenesis, *Science*, vol. 205, pp. 1010-1012 (1979).

Onosaka, S. et al., Concentration of Metallothionein in Malignant and Non-Malignant Tissues in Human Liver, *Eisei Kagaku*, vol. 30, pp. 173-176 (1984).

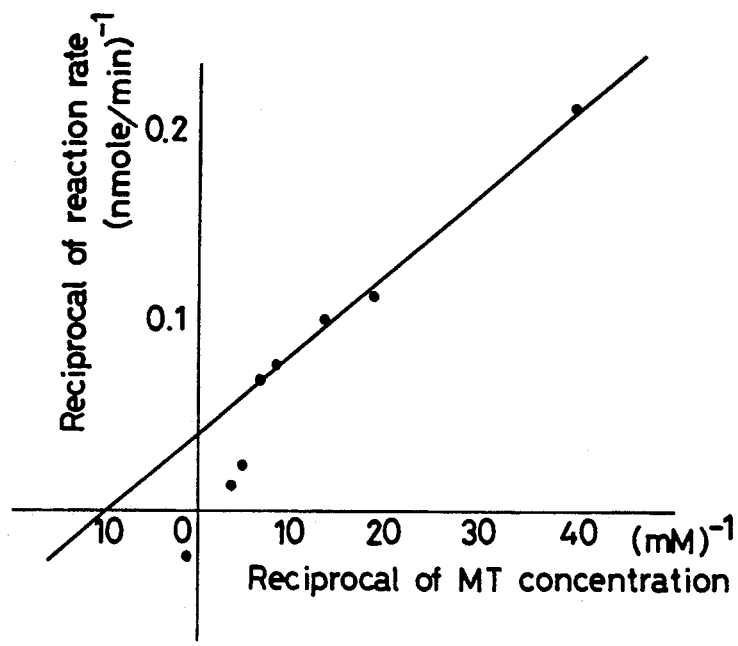
_Fig - 8_
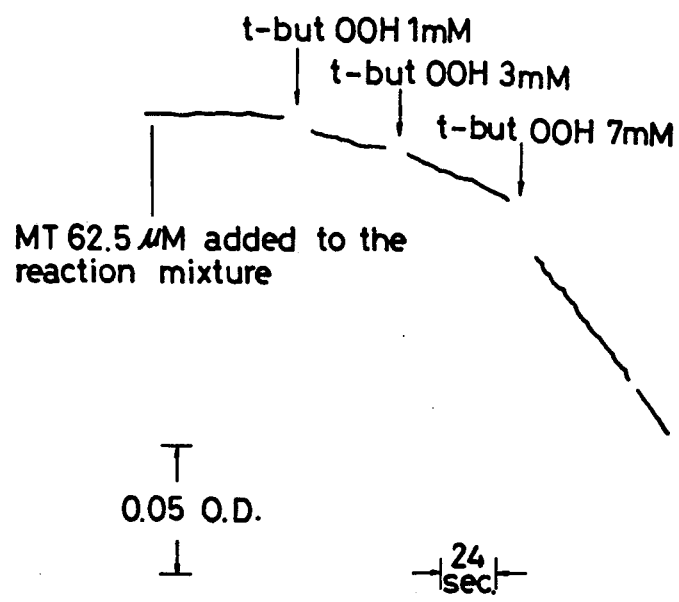
_Fig - 9_

METHOD OF USING MANGANESE TO PROTECT AN ANIMAL FROM RADIATION DAMAGE

TECHNICAL FIELD

This invention relates to a pharmaceutical agent acting on the protection mechanisms in human or animal bodies and, more particularly, to a pharmaceutical agent having activity of protecting living bodies from non-specific oxidative invasions thereof.

BACKGROUND OF THE INVENTION

Living bodies are exposed to a variety of environmental impacts. Such impacts are almost unlimited in number, including not only physical stimulations such as unceasingly arriving cosmic rays, radiations from the ground surface or buildings, ultraviolet rays in the sunlight and changes in ambient temperature but also chemical stimulations due to absorption of trace polutants in the air or foreign substances in foods and biological invasions by invisible viruses, bacterial, fungi, etc. Each living body is endowed with a very sophisticated and potent protection mechanism and it is this protection mechanism that allow the living organism to survive while overcoming those variegated invasions.

Fundamentally, the mechanism of living body damage by oxidative invasions from the environment and the defense mechanism are common in many aspects irrespective of differences in environmental factors. Thus, it is known that radiation damages, oxidant damages, inflammations, immunization, aging, carcinogenesis and various enzymatic processes are associated with free radical formation or active oxygen. It is also known that when many drugs act in human bodies, their metabolic processes involve free radical formation as a part thereof. Free radical formation is generally a factor harmful to healthy tissues except for its usefulness in some cases, for example in the case of microbicidal action of leukocytes or activation of certain enzymes in which $.O_2^-$ (superoxide radical) is physiologically involved. Living bodies have a nonspecific defense system against such free radical formation. More in detail, when a living body is exposed to a radiation or oxidant or to an action of a drug, such agent not only directly damages substances of biological importance, such as DNA, but also reacts with $O_2$ in the air to produce $.O_2^-$ or reacts with water ($H_2O$) in a tissue to form strongly reactive radicals such as $.OH$ (hydroxy radical). The $.O_2^-$ radical is partly eliminated as a result of conversion to $H_2O_2$ by SOD (superoxide dismutase) occurring in tissues. While catalase converts $H_2O_2$ to water and oxygen, $H_2O_2$ also reacts with $.O_2^-$ to form $.OH$, which has very high reactivity and attacks a variety of living-body substances. In particular, these reactions, via formation of lipid radicals, lead to peroxidation of unsaturated fatty acid components of phospholipids which are constituents of biomembranes. It is vitamin E that plays a definite role in blocking chain reactions involving those free radicals that are formed from such membrane lipids. When subjected to lipid peroxidation, biomembranes undergo polymerization and their functions are thereby disturbed. This results in temporary inhibition of different biochemical reactions or in abnormalities in the adrenocortical hormone activities. Damages of biomembranes due to the formation of lipid peroxides are prevented by the peroxide eliminating action of the glutathione (GSH)-peroxidase system (GP system).

As mentioned above, living organisms are subjected to various oxidative invasions from outside and inside. At the same time, however, the defense mechanism functions in them through the action of vitamin E and the radical- or peroxide-eliminating action of the above-mentioned SOD or GP system, among others. In case this defense mechanism fails to function satisfactorily, long-term effects of said invasions will result in such general phenomena as ischemic disorders of the brain or heart, damages of the lung and aging of cells. Such various radicals may damage DNA molecules directly and this may lead to carcinogenesis. Furthermore, a number of chemical carcinogens and intermediate metabolites include free radicals themselves or can activate free radicals. Thus, the problem of defense against free radicals and various disorders associated therewith is a problem of protection against carcinogenesis as well.

PRIOR ART

Any drug capable of effectively inhibiting and eliminating free radicals have not been developed as yet. The activity of vitamin E which is said to inhibit the formation of lipid radicals is not yet stable in effectiveness when evaluated from the system effect viewpoint. Thus, even a substance which has an effective activity on the cellular level cannot be used as a drug if it shows a severe side effect which may disturb the systemic balance. Generally drugs have to be used at doses lower than the doses at which their side effects pose a problem.

In cancer treatment, irradiation is generally used for the purpose of destroying cancer cell nuclei. Under the present conditions, however, few measures are taken against associated systemic adverse effects due to irradiation on other sites than the target sites.

In therapy and various industries dealing with radiations, a variety of means are taken to prevent workers from exotic exposure to radiations. However, any drugs effective in preventing radiation damages or reducing damages without causing adverse effects in case of exposure have not been developed as yet. Although cysteamine, S,2-aminoethylisothiuronium and S-2-(3-aminopropylamino)ethylphosphorothioic acid (WR-2721), among others, are known as sulfur-containing substances having an SH group which can function as protective substances against radiations and they are highly effective in preventing radiation damages in bone marrow stem cells, they are cytotoxic and produce very severe side effects. The margin between the toxic dose and effective dose is little. Therefore, they are hardly applicable to human bodies. As for glutathione which is effective in physiologically protecting organisms from radiations, its effect can be expected only at large doses since its entering cells is difficult and the retention time in the body is short (half-life: 2 minutes) even when it is administered from the outside.

As mentioned above, the defense mechanism in living bodies in which the above-mentioned SOD and GP systems play principal roles is the only measure relied upon in coping with disorders or damages of living bodies as resulting from free radical formation. At present, no particular means of actuating said mechanism of systematic viewpoint is employable as yet. However, when abnormal free radical formation is induced in the body, as in the case of irradiation particularly for cancer treatment, the defense mechanism which the living body itself has is no more sufficient but allows occurrence of various functional disorders such as mentioned above.

In view of such situation of the prior art, it is an object of the invention to provide a pharmaceutical agent capable of stimulating body's protection mechanism and inhibiting damages of living bodies as caused by various oxidative invasions such as exposure to radiations.

DISCLOSURE OF THE INVENTION

As a result of her intensive investigations to achieve the above object, the inventor found that metallothioneins (hereinafter referred to as MTs), which are metalloproteins, can be an alternative of glutathione which contribute to the inhibition of functional disorders due to biomembrane peroxidation and so forth, and that an antioxidative biophylaxis-potentiating activity, such as a protective activity against radiation damages, can be developed when MTs are induced in living organisms. The present invention has now been completed based on these findings.

Thus, the invention consists in an antioxidative biophylactic agent characterized in that it contains a substance capable of inducing MTs in living human or animal bodies.

MTs are low-molecular proteins having molecular weight of 6,000-7,000 and very rich in SH groups due to cysteine accounting for about one third of the constituent cells amino acids. They are known to be present in living body of various kinds from microorganisms to higher organisms. MTs contribute to alleviation of symptoms of intoxication from heavy metals such as Cd and Hg and estimatedly also play an important role in homeostasis of the concentration of Zn, which is one of essential elements, although their physiological activities have not yet been fully elucidated [M. Webb et al.: Biochem. Pharmacol., 31, 137 (1982); A. Karin: Cell, 41, 9 (1985)]. Furthermore, it is known that administration of Cd, Zn, Cu, Hg, Au and Ag induces MTs in tissues of living organisms ["Seitai to Jukinzoku (Living Organisms and Heavy Metals)", written and edited by Keiichiro Fuwa, published by Kodansha (1981)]. However, that MTs induced by a substance administered from the outside exhibit a protecting action against oxidative invasions in living organisms and that remarkable protective effects can be obtained by administration of the substances mentioned below are the finding obtained for the first time by the inventor.

Thus, those metals so far known to be capable of inducing MTs, such as cadmium, zinc, copper, mercury, gold and silver, or compounds of such metals can be used as the substance capable of inducing MTs in the practice of the invention. The inventor found that manganese and compounds thereof, hemolytic streptococci (*Streptococcus haemolyticus*) treated for elimination of the streptolysin S production capacity (hereinafter referred to simply as hemolytic streptococci), and an extract of *Coriolus versicolor* Quel, which belongs to the order Polyporales of the class Basidiomycetes, have marked MT-inducing capacity and exhibit marked antioxidative and biophylaxis-potentiating activity, for example protective activity against radiation damages.

In the case of application to human bodies, manganese, zinc and gold and compounds of these, the above-mentioned hemolytic streptococci and the above-mentioned *Coriolus versicolor* extract are preferable from the toxicity viewpoint, and manganese and compounds thereof, the above-mentioned hemolytic streptococci and the above-mentioned *Coriolus versicolor* extract are preferable particularly from the efficacy viewpoint. As manganese, water-soluble manganese salts are more preferably used.

Hemolytic streptococci constitute a class of streptococci capable of producing streptolysin, a hemolytic toxin, and are pathogenic bacteria causing erysipelas, septicemia, puerperal sepsis, tonsillitis and various other diseases. However, it is known that they can be applied to human bodies after elimination of their ability to produce streptolysin S which is stable against oxygen (Japanese Patent Laid-open Publication No. 56-79622).

In the practice of the invention, any strains of hemolytic streptococci can be used if the streptolysin S production capacity has been eliminated. The term "hemolytic streptococci" as used herein includes various kinds of cells treated in an appropriate manner, such as the strains *Streptococcus pyogenes* Su (ATCC 21060), *Streptococcus pyogenes* C203S (ATCC 21546), *Streptococcus pyogenes* S-43 (ATCC 21547), *Streptococcus pyogenes* Black-more (ATCC 21548) and *Streptococcus equisimilis* (ATCC 21597), each treated in various ways.

A typical method for the elimination of the streptolysin S production capacity of these bacterial cells comprises suspending viable cells in a salt solution, for example Bernheimer's basal medium (BBM), containing penicillin at a relatively high concentration and maintaining the suspension at 30°-38° C. [Jpn. J. Exp. Med., 36, 161-171 (1966)]. A method which comprises treating the suspension further at 40°-50° C. (Japanese Patent Publication No. 43-6690) can also be used. Furthermore, the use of cephalosporin C or cycloserine in lieu of penicillin gives equivalent results (British Patent No. 1,153,113; Japanese Patent Publications No. 45-8871 and No. 46-2674). In addition, preparations containing a smaller number of viable cells can be obtained by treating with hydrogen peroxide or a monohydric alcohol in the above process step (Japanese Patent Publication No. 55-43754; Japanese Patent Laid-Open Publication No. 57-18621).

L-Group hemolytic streptococci which are obtainable by cultivating cells of a hemolytic streptococcal strain under conditions such that the cell wall synthesis is inhibited, for example in a penicillin-containing hypertonic medium or by treating hemolytic streptococcal cells with a bacteriolytic enzyme and then cultivating said cells in a medium containing an inhibitor of cell wall synthesis such as penicillin are known to be free of such drawbacks as phlegmogenicity, pyrogenicity and pain-causing property and can be used as preferable streptococcal cells as well (Japanese Patent Laid-Open Publication No. 56-15210).

A particularly preferred hemolytic streptococcal preparation usable in the practice of the invention is composed of cells of the attenuated, human-derived A hemolytic streptococcal strain *Streptococcus pyogenes* Su as treated with penicillin G potassium, and a cell preparation obtained by lyophilizing said cells is known as OK-432. OK 432 is a lyophilizate derived from a treated culture product obtained by cultivating the above-mentioned cells in Bernheimer's basal medium containing penicillin G potassium (not less than 25,000 units/ml, preferably 27,000-60,000 units/ml) at 30°-38° C. (preferably 37° C.) for 10-30 minutes (preferably 20 minutes) and then incubating at 30°-50° C. (preferably 45° C.) for 20-40 minutes (preferably 30 minutes), with hydrogen peroxide treatment being performed in the meanwhile and occurs as a white to almost white, hygroscopic lyophilizate powder containing a stabilizer. Its suspension formed upon addition of physiological saline has a pH of 5.5-7.5, with an osmotic pressure ratio of 1 relative to physiological saline. OK-432 shows no streptolysin S production capacity but shows disappearance of the capsule and partial damage of the cell wall as compared with the starting material viable Su strain cells. The $LD_{50}$ value in dogs is 36 KE/kg (1 KE corresponding to 0.1 mg of lyophilized cells). For the method of production, properties, biological characteristics, pharmaceutical characteristics such as toxicity, and physiological activities of OK-432, refer to Nakao Ishida and Takashi Hoshino: "Hemolytic Streptococcal Preparation OK-432", published by Excerpta Medica (1985).

The *Coriolus versicolor* extract can be used in the form of a fraction obtained, for example, by extracting mycelia of *Coriolus versicolor* Quel with hot water, saturating the supernatant with ammonium sulfate, collecting the resultant precipitate and desalting the same. Said fraction is known as PS-K [Shigeru Tsukagoshi: Gan to Kagaku Ryoho (Cancer and Chemotherapy), 1, 251-257 (1974); Igaku no Ayumi (Advaces in Medicine), 91, 505-510 (1974)]. This PS-K is a glycoprotein containing 19 kinds of amino acids inclusive of aspartic acid and glutamic acid with a protein content of about 15% and is known to have low toxicity.

The antioxidative biophylactic agent according to the invention is useful typically as a protective agent against radiation damages due to radiations such as X rays, alpha rays, beta rays, gamma rays, neutron beams, accelerated electron beams and ultraviolet rays. The above-mentioned hemolytic streptococci and *Coriolus versicolor* extract are known to have antitumor activity and, when they are used on the occasion of radiotherapy for cancer treatment, they should preferably have a high degree of antitumor activity and, in this case they can be subjected to various treatments for increasing the antitumor activity in addition to the above-mentioned treatments to increase more potentiality to induce MTs.

The antioxidative biophylactic agent according to the invention can be administered either orally or non-orally in the form of the above-mentioned substance capable of MT induction as it is or in dosage forms such as powders, granules, tablets, capsules or injections prepared by admixing said substance with pharmaceutically acceptable diluents, excipients, carriers and/or the like. The dose may vary greatly depending on the specific purpose of use as an antioxidative biophylactic agent, the MT induction capacity of the above-mentioned substance, the target of administration, the route of administration, and other factors, hence cannot be particularly limited. Generally, however, it amounts to 0.1-1,000 mg/kg of body weight per administration. In cases where it is used for preventing radiation damages, it should desirably be administered about one day prior to irradiation. The protective effect of water-soluble manganese on radiation damages is remarkable and, in this case, a salt containing the divalent Mn ion, such as manganese chloride or manganese sulfate, is desirably administered at a dose of 10-30 mg of Mn per kilogram of body weight. The above-mentioned hemolytic streptococci and *Coriolus versicolor* extract also have remarkable protective activity against radiation damages and, in this case, an optimum dose per administration is roughly within the range of 0.1-10 mg/kg body weight in the case of hemolytic streptococci and 10-1,000 mg/kg body weight in the case of *Coriolus versicolor* extract.

BRIEF DESCRIPTION OF THE DRAWINGS

FIG. 8 is a graph for determining the Km value for the action of the MT on the GP system.

FIG. 9 is a graph illustrating the site of action of the MT on the GP system.

WORKING EXAMPLES

The pharmacological activities of several antioxidative biophylactic agent according to the invention are illustrated in the following examples.

I. ANTIOXIDATIVE BIOPHYLACTIC ACTIONS WHICH MT-INDUCING SUBSTANCES EXERT

Since, as mentioned above, the mechanism of living body damaging due to oxidative invasions and the protective mechanism are fundamentally common in large part irrespective of the damage-causing factor, a particular case of radiation damaging is given herein as a typical example.

TEST EXAMPLE 1 (EFFECTS OF VARIOUS METALS)

Manganese (Mn), cadmium (Cd) and zinc (Zn) were administered to mice beforehand and the whole body each mouse was then irradiated with X rays. The body weight changes and mortality rates were recorded and the liver MT levels were determined.

(1) Method

The animals used were ddY-strain clean male mice (7 weeks of age). $MnCl_2$ (10 mg Mn/kg body weight), $CdCl_2$ (3 mg Cd/kg body weight) or $Zn(CH_3COO)_2$ (20 mg Zn/kg body weight) was dissolved in 0.9% aqueous sodium chloride solution and given to the mice by subcutaneous injection each at a dose not higher than the semilethal dose. After 24 hours, the mice were irradiated with X rays at a dose of 630 rad almost corresponding to the $LD_{50}$. Thereafter, the body weight changes in the mice and the mortality rates were recorded for 30 days. At the same time, the mouse liver was excised 24 hours after administration of those metals, namely immediately before X ray irradiation, and 24 hours after X ray irradiation and the MT content in each liver homogenate was determined by the Cd hemoglobin saturation method of Onosaka et al. [Eisei Kagaku (Hygienic Chemistry), 24, 128-131 (1978)].

(2) Results

Figure 1:
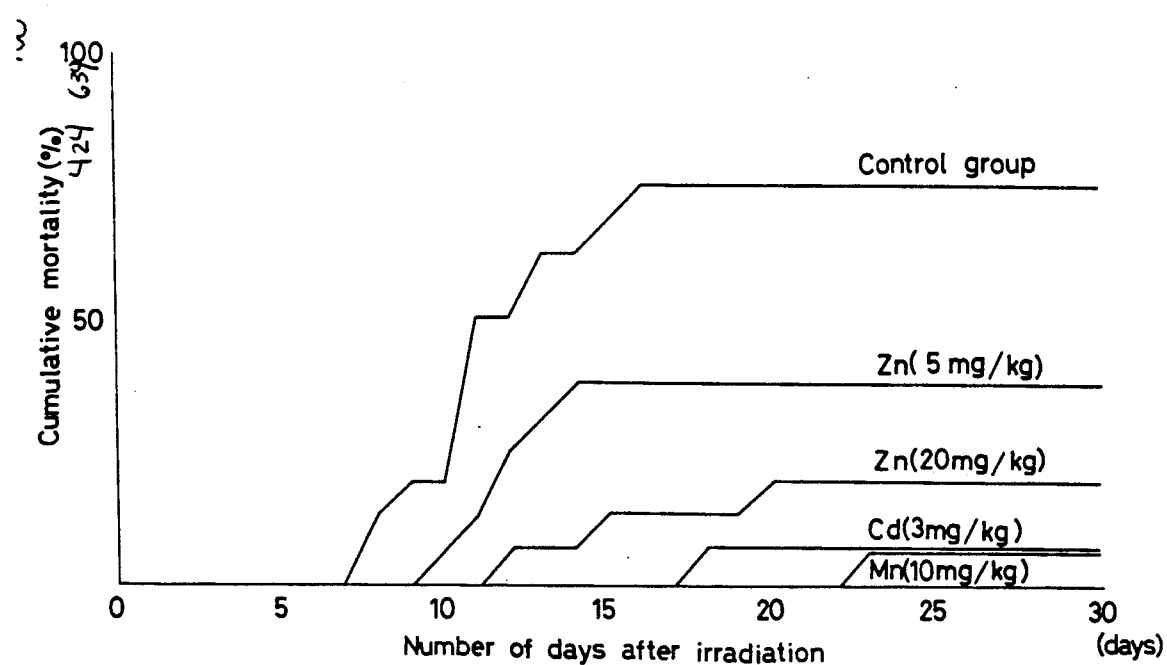
FIG. 1 is a graphic representation of the cumulative mortalities in mice of metal-dosed and other groups after irradiation with 630 rad of X rays.
Figure 2:
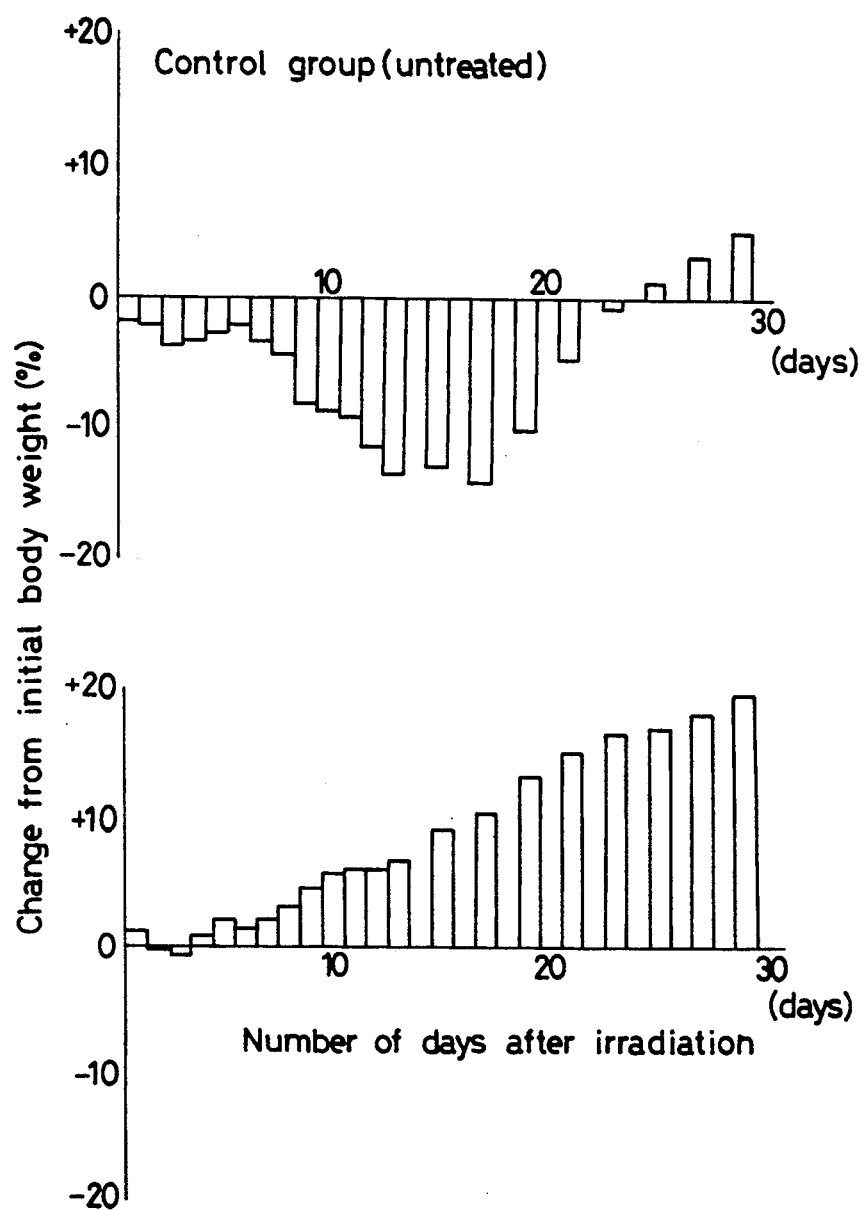
FIG. 2 is a graphic representation of the changes in body weight in mice of Mn-dosed and other groups after irradiation of 630 rad of X rays in the same test example.

The cumulative mortalities in mice of the respective groups after irradiation with 630 rad of X rays are shown in FIG. 1. In all the metal-dosed groups, namely the Mn, Cd and Zn groups, reductions in radiation-induced mortality were found as compared with the control (undosed) group. In each of the Cd- and Mn-dosed groups, in particular, the cumulative mortality was 0.06, namely not higher than one tenth of that in the control group, namely 0.75. It was thus confirmed that preliminary administration of Mn or Cd can reduce radiation damages remarkably. The changes in mouse body weight as followed on that occasion for 30 days revealed a typical two peak body weight decrease curve characteristic of radiation damages for the control group whereas, in the Mn-dosed group, the body weight decrease was almost negligible but, contrariwise, the body weight continued to increase even after irradiation and the general condition of mice as evaluated on the basis of the appearnce of the coat of fur, the condition of anemia and the body movement was obviously good. In the Cd-dosed group, typical body weight loss supposedly due to the toxicity of Cd itself was observed at the first week of post irradiation but mice could survive and the general condition was good as in the Mn-dosed group. On the other hand, individual differences in body weight change were great in the Zn-dosed group although a reduction in mortality was observed, as shown in FIG. 1. The fact that, in the case of Mn, a protective effect can be produced at a dose not more than one twentieth of the semilethal dose but that, in the case of Cd or Zn, a dose of about one half to one third of the semilethal dose is required may be associated with the above fact.

The MT levels in the liver as determined 24 hours after the pretreatment i.e. exactly before X-ray irradiation and 48 hours after the pretreatment i.e. 24 hours after irradiation in mice are shown in Table 1.

TABLE 1

| | | MT concentrations in mouse liver ($\mu$g/g liver tissue) | |
|---|---|---|---|
| | | Mean ± standard deviation | |
| Pretreatment | | Before irradiation (24 hours after pretreatment) | After irradiation (48 hours after pretreatment) |
| CdCl$_2$ | 3 mg Cd/kg s.c. | 198 ± 41 | 563 ± 38 |
| Zn-acetate | 5 mg Zn/kg s.c. | 33 ± 5 | 88 ± 25 |
| Zn-acetate | 20 mg Zn/kg s.c. | 120 ± 18 | 189 ± 24 |
| MnCl$_2$ | 10 mg Mn/kg s.c. | 126 ± 16 | 156 ± 38 |
| Physiological saline | 5 mg/kg s.c. | 25 ± 1 | 66 ± 14 |
| Undosed | | 26 ± 1 | 71 ± 22 |

About five- to seven-fold increases MT level in mouse liver immediately before X ray irradiation were confirmed in the groups given 20 mg/kg body weight of Zn, 3 mg/kg body weight of Cd and 10 mg/kg body weight of Mn, respectively, as compared with the control group level of 26±1 $\mu$g/g liver tissue. Furthermore, the mouse liver MT levels after X-ray irradiation show increases by not less than several tens of micrograms per gram as compared with the levels before irradiation in the dosed groups as well as in the undosed group. Similarly, sub-cutaneous injection of 1.25 mg/kg body weight of Cu resulted in an increase in mouse liver MT level to 118±21 $\mu$g/g liver tissue. In contrast to these results, salts incapable of MT induction, such as Mg salts, did not show any protective action against radiations.

TEST EXAMPLE 2 (EFFECTS OF THE DOSE OF Mn)

(1) Method

The procedure of Test Example 1 was followed except that the dose of Mn was varied within the range of 5-50 mg Mn/kg and that the irradiation was performed at a semilethal dose of 630 rad and at a lethal dose of 720 rad.

(2) Results

Figure 3:
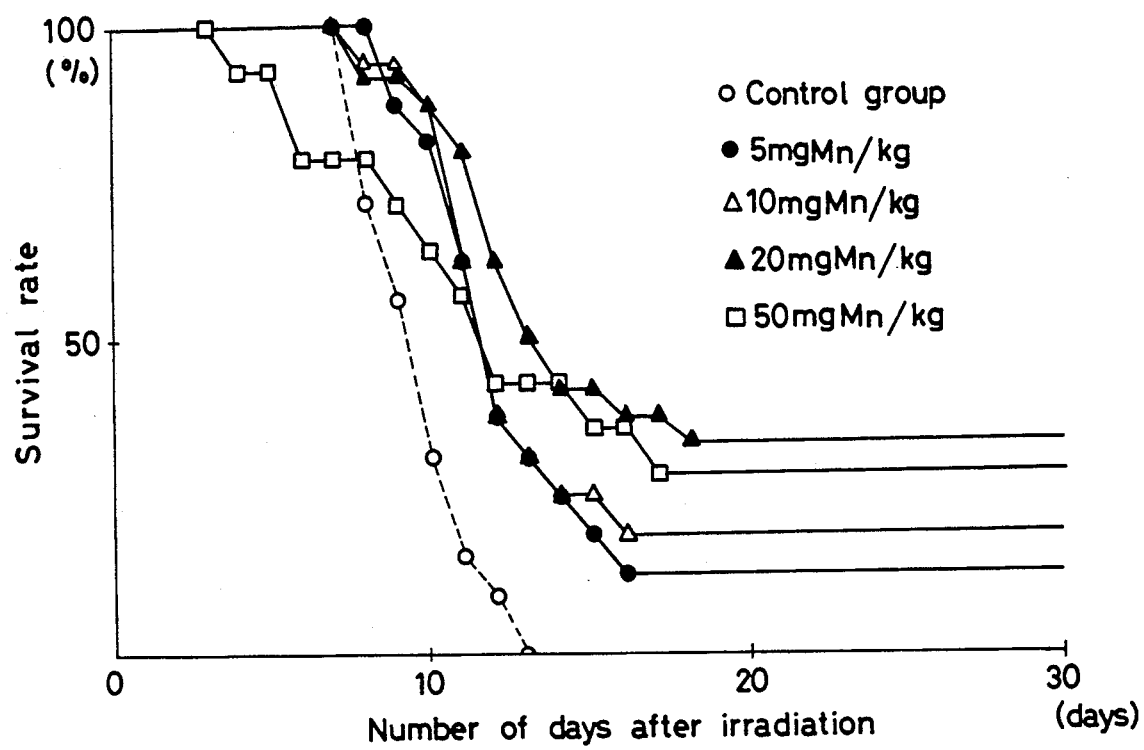
FIG. 3 is a graphic representation of the survival rates in mice of different Mn-dosed groups after irradiation with 720 rad of X rays.

The mortalities for the respective mouse groups after irradiation with 720 rad of X rays are shown in FIG. 3 and the liver MT levels 24 hours after irradiation are shown in Table 2. It was confirmed that, as shown in Table 2, the liver MT level increases with the increase of the dose of Mn and that, as shown in FIG. 3, the survival rate increases as well with the increase of the dose of Mn within the range of 5-20 mg Mn/kg. The decrease of the survival rate in the case of 50 mg Mn/kg is supposedly due to the toxicity of Mn itself.

TABLE 2

| MT formation versus dose of Mn | |
|---|---|
| Dose of Mn (mg Mn/kg) | Liver MT concentration (nmol/g tissue) |
| 0 (control) | 3.01 ± 0.08 |
| 5 | 4.55 ± 0.80 |
| 10 | 13.30 ± 2.82 |
| 20 | 24.38 ± 6.61 |
| 50 | 29.13 ± 2.70 |

Figure 4A:
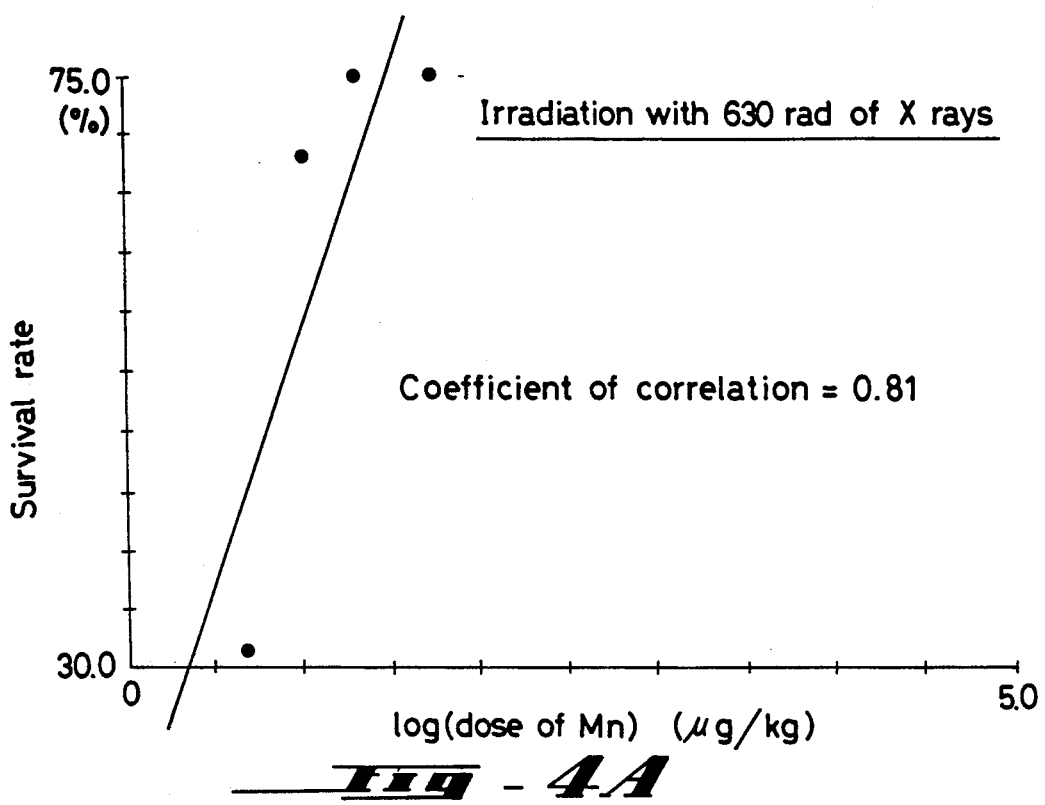
FIG. 4A and FIG. 4B are graphic representations of the relationship between the survival rate in mice of each group after irradiation with 630 rad of X rays and the dose of Mn and the relationship between said survival rate and the logarithm of the liver MT concentration, respectively, each with a coefficient of correlation as determined by simple regression analysis.
Figure 4B:
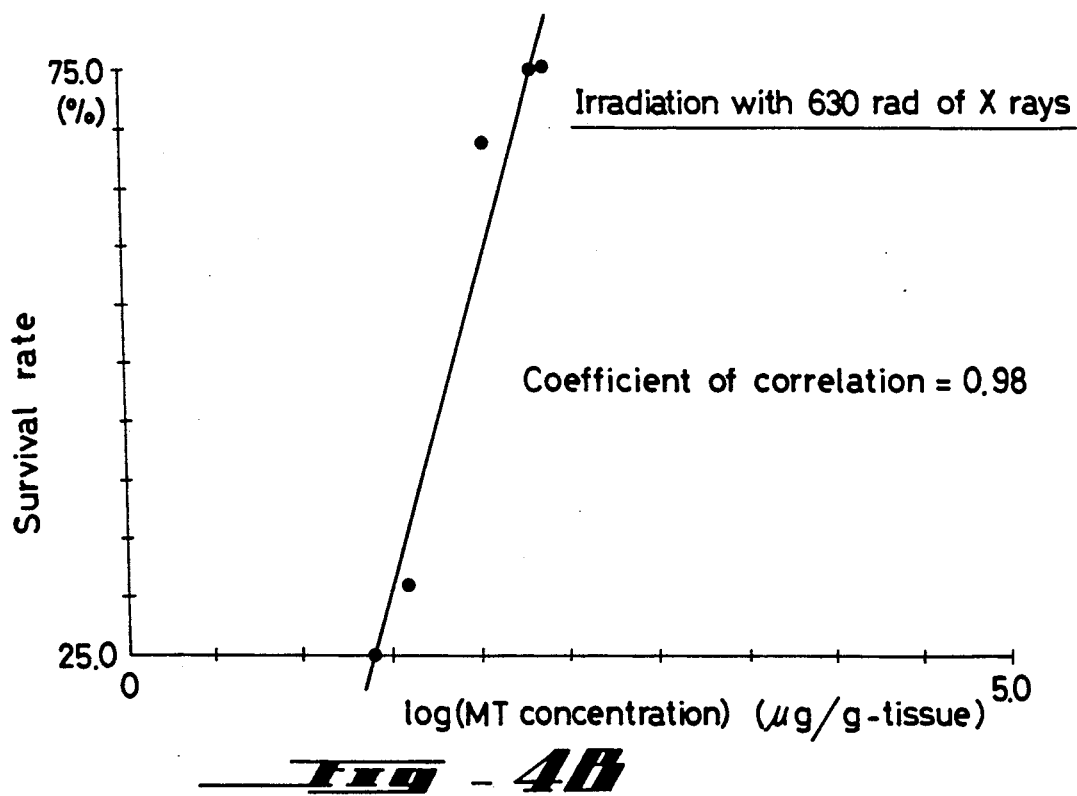

The relation between the survival rate in each group of mice after irradiation with 630 rad of X rays and the dose of Mn and the relation between said rate and the logarithm of the liver MT concentration are shown in FIG. 4A and FIG. 4B, respectively, with the coefficients of correlation as found by simple regression analysis. The results indicate that the mouse survival rate is directly correlated with the MT concentration in the liver rather than with the dose of Mn.

TEST EXAMPLE 3 (EFFECT OF Zn VERSUS RADIATION DOSE)

Water containing the Zn ion in a high concentration (1,000 ppm) was preadministered to mice, the mice were then subjected to whole-body irradiation with gamma rays, and the biophylactic effect versus the radiation dose was investigated.

Figure 5:
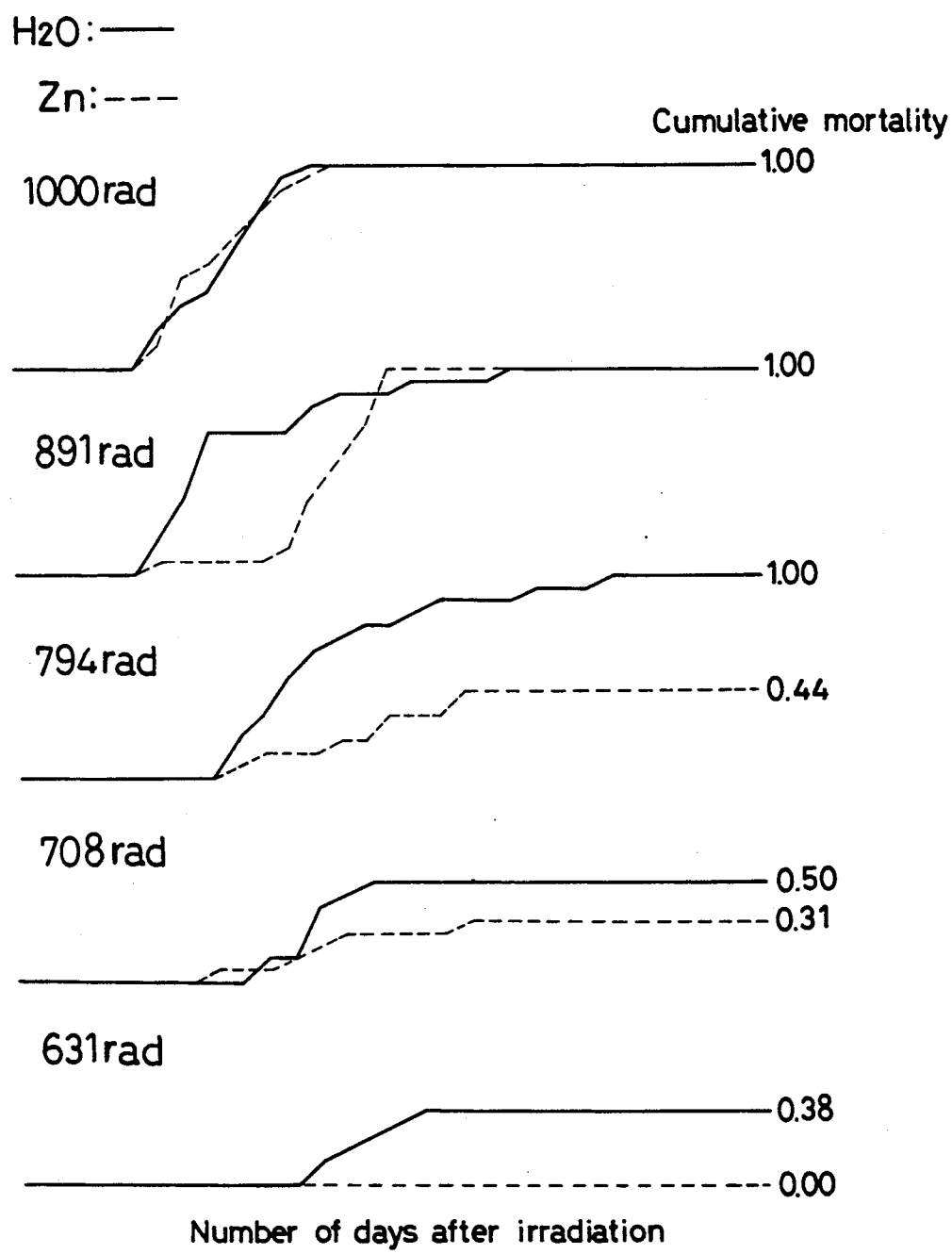
FIG. 5 is a graphic representation of the cumulative mortalities in relation to the number of days after irradiation with gamma rays in mice drinking zinc-containing water.

FIG. 5 shows the cumulative mortality versus the number of days after irradiation of mice given Zn-containing drinking water with gamma rays at a semilethal or lethal dose. A decrease in mortality and a life span prolonging effect were observed in the Zn-drinking group as compared with the control group. The results also indicate that the effect of irradiation is not weakened when the radiation dose is large and equals or exceeds the lethal dose but that a biophylactic effect is produced when the radiation dose is lower.

TEST EXAMPLE 4 (MT INDUCTION BY HEMOLYTIC STREPTOCOCCI AND BY A *CORIOLUS VERSICOLOR* EXTRACT)

OK-432 (Chugai Pharmaceutical Co.; trademark Picibanil) and PS-K (Sankyo Pharmaceutical Co.-Kureha Chemical Industry Co.; trademark Krestin) were respectively administered to mice and liver MT concentrations were determined. For comparison, MT-inducing metals such as cadmium (Cd), zinc (Zn) and manganese (Mn) were also administered.

(1) Method

The animals used were Jcl:ICR-strain male mice (7 weeks old and 9 weeks old). They had free access to diet and water and were fed in a constant-temperature environment. The agents shown in Table 1 were administered either singly or continuously at one- or two-day intervals in the dosage and manner indicated in the table and, 20 hours later, the liver MT levels were determined. The assay of MTs was performed by the Cd-hemoglobin saturation method of Onozaki et al. [Eisei Kagaku, 24, 128-131 (1978)] and by the Ag-hemoglobin saturation method of Cherian et al. [Toxicol., 23, 11-20 (1982)].

(2) Results

While the mouse liver MT concentration in untreated mice of 4 to 25 weeks of age generally amounts to about 2-3 nmol/g, OR-432 and PS-K, in both the cases of single administration and prolonged administration, gave values several times higher as compared with mice in the control group and thus each showed a high MT induction capacity comparable to that found in metal administration.

(2) Results

Figure 6:
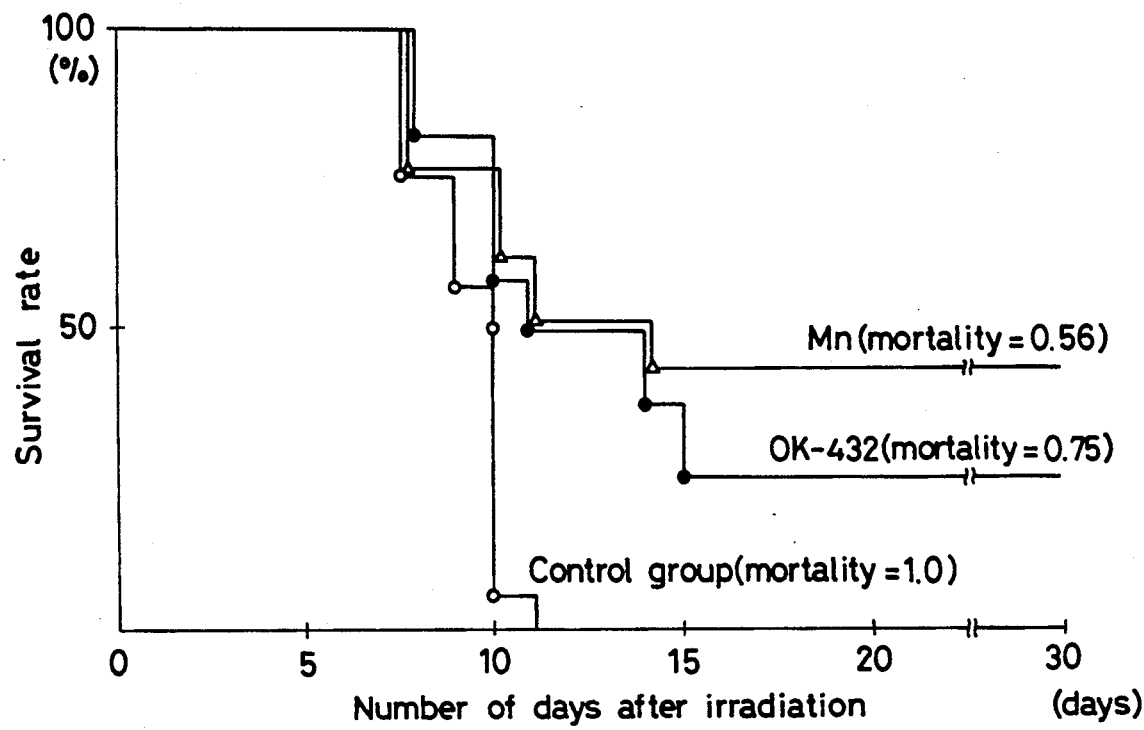
FIG. 6 is a graphic representation of the survival rates in mice of an OK-432-dosed group after irradiation with 720 rad of X rays, which is the lethal dose.

The survival rates of the respective groups of mice after irradiation with 720 rad of X rays are shown in FIG. 6. The data confirmed that reductions in the rate of deaths due to irradiation as compared with the control (undosed) group are found in the OK-432 and Mn groups and that a radiation damage reducing activity which is comparable to that of Mn preadministration can be obtained by preadministration of OK-432.

II. ACTION IN THE ANTIOXIDATIVE BIOPHYLAXIS MECHANISM IN WHICH MTs ARE INVOLVED

As already mentioned hereinabove, the glutathione (GHS)-peroxidase system (GP system) plays an important role in the antioxidative biophylaxis mechanism in living organisms. In the GP system shown in FIG. 7, GSH-peroxidase (GP) reduces peroxides. For the reduction, GSH is required as an electron donor, and, as a result, GSH is converted to oxidized-form glutathione (GSSG). Since the oxidized GSH, namely GSSG, is apt to flow out of the cell, it is naturally conceivable that intracellular GSH might sometimes become insufficient in quantity In fact, it has been observed that the susceptibility to radiations increases when the GSH level is decreased [Ohara et al.: Exp. Cell. Res., 58, 182-185 (1970); Modig et al.: Int. J. Radiat. Biol., 22, 258-268 (1971); etc.]. It has also been reported that a reduction in GSH level leads to reduced resistance to radiations upon exposure thereto as well as to various pathological phenomena such as ulceration in the stomach, canceration of cells and hemolysis [Boyd et al.: Science, 205, 1010-1012 (1979); etc.].

TABLE 3

NT formation in the mouse liver after various kinds of pretreatment

| | Pretreatment | Age of mice (weeks) | Liver MT concentration (nmol/g tissue) | |
|---|---|---|---|---|
| | | | Cd-hem method | Ag-hem method |
| OK-432 | 10 KE/animal × once, i.p. | 7 | 14 ± 5 | 13 ± 5.6 |
| | 1 KE/aminal × 10 times, i.p. | 9 | 19 ± 11 | |
| PS-K | 50 mg/kg × once, i.p. | 7 | 5.7 ± 1.1 | |
| | 50 mg/kg × 9 times, i.p. | 9 | 22 ± 9.3 | |
| CdCl$_2$ | 3 mg Cd/kg × once, s.c. | 7 | 25 ± 5.0 | |
| Zn-acetate | 20 mg Zn/kg × once, s.c. | 7 | 15 ± 2.3 | |
| MnCl$_2$ | 10 mg Mn/kg × once, s.c. | 7 | 16 ± 2.0 | |
| physiological saline | 6.7 ml/kg × once, i.p. | 7 | 2.8 ± 1.0 | 1.7 ± 0.2 |
| | 6.7 ml/kg × 10 times, i.p. | 9 | 1.5 ± 0.4 | |

Each result given is the mean of 5 animals, accompanied by the standard deviation.

TEST EXAMPLE 5 (PROTECTIVE ACTION OF HEMOLYTIC STREPTOCOCCI AGAINST IRRADIATION)

OK-432 (Chugai Pharmaceutical Co.; trademark Picibanil) was preadministered to mice, whole-body X ray irradiation was then conducted, and the survival rate after irradiation was recorded. Its activity was compared with that of manganese (Mn).

(1) Method

The animals used were Jcl:ICR-strain male mice (7 weeks of age). OR-432 (5 KE/animal) and MnCl$_2$ (20 mg Mn/kg body weight) were respectively dissolved in 0.9% aqueous sodium chloride solution, and OK-432 was given by intraperitoneal injection and MnCl$_2$ by subcutaneous injection. One day later, the dosed groups, together with a control group, were irradiated with the lethal dose of 720 rad of X rays, and the survival rates were recorded for the subsequent 30 days.

The inventor confirmed that, like GSH, MTs can work as the alternative of GSH to react with GP. This is illustrated in detail in the following.

(1) Method

Figure 7:
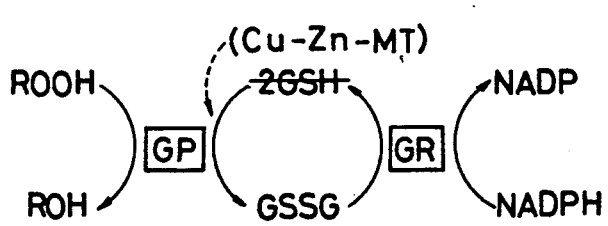
FIG. 7 is a schematic representation of reactions for illustrating the involvement of copper-zinc-thionein in the glutathione-peroxidase (GP) system.

To examine whether MTs can serve as electron donors to the GP system, namely as substitutes for GSH, under conditions in which GSH is absent, an in vitro system shown in FIG. 7 was constructed. Thus, the reduction of the substrate t-butyl-OOH by GP was put in the coupled NADPH oxidation system, as shown in FIG. 7, and the change of absorbance at 340 nm as caused by consumption of NADPH in the reaction mixture in a cuvette was followed using a double-beam spectrophotometer. The procedure was as follows: Two cuvettes for the spectrophotometer are filled with the following solution in exactly the same volume. The reaction mixture solution is principally 250 mM (hereinafter each concentraiton being a final concentration) phosphate buffer (pH 7.4) with NaN$_3$ added to a concentration of 2.5 mM and further supplemented with 0.3 unit/ml each of GP and glutathione reductase (GR), 5 mM t-butyl OOH and 0.5 mM NADPH, for both cuvettes. Finally, GSH or MT is added to one of the cuvettes, when the reaction starts, and the difference in absorbance between the cuvettes is observed of a recorder. In this way, the decrease in the quantity of NADPH per unit time (rate of reaction) is observed. By increasing the concentration of GSH or MT stepwise (titration), the Km value (Michaelis constant) for the enzymatic reaction of GP can be determined.

(2) Results

FIG. 8 shows the results of the Km value measurement for MT to GP by stepwise addition of MT, as alternative to GSH, to the GP system. It was repeatedly confirmed that the Km value for MT as determined on the basis of the Lineweaver-Burke plots shown in the figure is in the order of 0.1 mM. On the other hand, the Km value for GSH was about 4 mM. The MT used was copper-zinc-thionein purified from the calf liver. When, in the reaction shown in FIG. 7, GP, GR and NADPH are first added to the reaction mixture and then MT is added, no reaction is started. On the contrary, when t-butyl-OOH is added thereto, the reaction starts, as shown in FIG. 9. This indicates that MT serves as an electron donor to the GP system, not to GR.

While the MT level in cells may vary over a wide range of 7-500 μg/g wet tissue, the liver MT level in normal mice, when measured by the inventor, differed little according to sex or age (in weeks) and was about 20 μg/g, that is about 3 μM, but increased to 120 to hundreds of micrograms per gram (20-100 μM) upon stress loading such as metal administration. The liver MT level in human is higher than in animals and, according to a report of Onozaka et al., it is 200-550 μg/g [Onozaka et al.: Eisei Kagaku, 30, 173-176 (1984)]. The Km value for copper-zinc-thionein to GP as determined by the inventor is about 100 μM and therefore this reaction is considered to be able to proceed physiologically when MTs are sufficiently induced and synthesized in living organisms.

INDUSTRIAL APPLICABILITY

As described hereinabove, the antioxidative biophylactic agent according to the invention induces metallothioneins (MTs) in living organisms and these MTs cause the biophylactic function to be performed in lieu of glutathione (GSH). Therefore, said agent does not inhibit free radical formation or eliminate free radicals in a direct manner upon oxidative invasions such as irradiation but prevent various functional disorders due to biomembrane damages and increases the resistance and recovery of cells. In particular, manganese and compounds thereof, hemolytic streptococci and *Coriolus versicolor* extracts are remarkably effective. Among others, OK-432 and PS-K have already been applied to human bodies as antitumor agents and accordingly their safety has been confirmed. Therefore, in cases where the possibility of exposure to radiations will increase in the future, for example in the case of workers in the nuclear power industry, astronauts working in the cosmic field, workers in the medical field who are engaged in diagnosis and treatment of such diseases as cancer, or patients who have to be exposed to undesirable irradiation for the purpose of diagnosis, the biophylactic function in human bodies can be promoted by administering said agent in advance as a prophylactic means of preventing possible radiation damages.

What is claimed is:

1. A method of protecting a host from radiation damage, comprising administering to a host in need thereof an effective radiation damage protecting amount of a water-soluble manganese salt in an amount effective to increase the liver metallothionein level in the host by at least fivefold within about one day following the administration.

2. The method of claim 1, wherein the water-soluble salt is administered to the host at about 5-30 mg manganese per kg body weight of the host.

3. The method of claim 1, wherein the water-soluble salt is administered to the host at about 10-20 mg manganese per kg body weight of the host.

4. The method of claim 1, wherein the water-soluble manganese salt is administered to the host orally or by injection.

UNITED STATES PATENT AND TRADEMARK OFFICE
CERTIFICATE OF CORRECTION

PATENT NO. : 5,008,119
DATED : April 16, 1991
INVENTOR(S) : J. Matsubara It is certified that error appears in the above-identified patent and that said Letters Patent is hereby corrected as shown below:

| COLUMN | LINE | |
|---|---|---|
| 1 | 21 | Delete "bacterial" and insert therefor --bacteria-- |
| 4 | 55-56 | Delete "A hemolytic" and insert therefor --A-hemolytic-- |
| 4 | 59 | Delete "OK 432" and insert therefor --OK-432-- |
| 5 | 22 | Delete "Advaces" and insert therefor --Advances-- |
| 7 | 19 | Delete "two peak" and insert therefor --two-peak-- |
| 7 | 25 | Delete "appearnce" and insert therefor --appearance-- |
| 10 | 67 | Delete "concentraiton" and insert therefor --concentration-- |
| 11 | 3 | Delete "t-butyl OOH" and insert therefor --t-butyl-OOH-- |
| 11 | 37 | Delete "human" and insert therefor --humans-- |
| 12 | 34 | After "least" insert --about-- |

Signed and Sealed this

Fifteenth Day of December, 1992

*Attest:*

DOUGLAS B. COMER

*Attesting Officer*  *Acting Commissioner of Patents and Trademarks*